US010152150B2

(12) United States Patent
Sherman

(10) Patent No.: US 10,152,150 B2
(45) Date of Patent: *Dec. 11, 2018

(54) FACILITATING USER INPUT VIA ARM-MOUNTED PERIPHERAL DEVICE INTERFACING WITH HEAD-MOUNTED DISPLAY DEVICE

(71) Applicant: John Sherman, Peachtree City, GA (US)

(72) Inventor: John Sherman, Peachtree City, GA (US)

(*) Notice: Subject to any disclaimer, the term of this patent is extended or adjusted under 35 U.S.C. 154(b) by 792 days.

This patent is subject to a terminal disclaimer.

(21) Appl. No.: 14/711,933

(22) Filed: May 14, 2015

(65) Prior Publication Data

US 2015/0269324 A1 Sep. 24, 2015

Related U.S. Application Data

(63) Continuation of application No. 14/473,894, filed on Aug. 29, 2014, now Pat. No. 9,053,654.

(Continued)

(51) Int. Cl.
*G06F 19/00* (2018.01)
*G06F 3/041* (2006.01)
(Continued)

(52) U.S. Cl.
CPC ........... *G06F 3/041* (2013.01); *G02B 27/017* (2013.01); *G06F 1/163* (2013.01); *G06F 3/005* (2013.01); *G06F 3/011* (2013.01); *G06F 3/0227* (2013.01); *G06F 3/03547* (2013.01); *G06F 3/04817* (2013.01); *G06F 19/3418* (2013.01); *G06F 19/3468* (2013.01); *G09G 5/003* (2013.01); *G16H 10/60* (2018.01);
*G16H 10/65* (2018.01); *G16H 40/63* (2018.01); *G02B 2027/0178* (2013.01); *G06F 3/147* (2013.01); *G06F 9/453* (2018.02); *G06F 2203/0381* (2013.01);
(Continued)

(58) Field of Classification Search
CPC ............. G02B 2027/0178; G06F 1/163; G06F 2203/04104
USPC .......................................................... 705/3
See application file for complete search history.

(56) References Cited

U.S. PATENT DOCUMENTS 7,470,244 B2 12/2008 Harrison, Jr.
9,053,654 B2 6/2015 Sherman
(Continued)

*Primary Examiner* — Victoria P Shumate
*Assistant Examiner* — Teresa S Williams
(74) *Attorney, Agent, or Firm* — Tillman Wright, PLLC; Chad D. Tillman

(57) ABSTRACT

An apparatus for performing data entry by a user includes a first electronic device configured to be attached to a person's head and including a display for viewing by the person; and a second electronic device configured to be attached to a person's forearm and used in combination with the first electronic device. The first and second electronic devices are configured for wirelessly communications with each other, at least some of the wireless communications representing user input by the person for interfacing with a user interface displayed to the person on the display of the first electronic device, whereby data entry by the person is accomplished. The first electronic device is configured to wirelessly transmit data entered by the person to a computer system for electronic storage in a non-transitory computer readable medium.

20 Claims, 8 Drawing Sheets

Finger-Flexed Position

Related U.S. Application Data

(60) Provisional application No. 61/884,344, filed on Sep. 30, 2013.

(51) Int. Cl.
| | | |
|---|---|---|
| *G09G 5/00* | (2006.01) | |
| *G06F 3/02* | (2006.01) | |
| *G06F 3/00* | (2006.01) | |
| *G06F 3/0354* | (2013.01) | |
| *G06F 3/01* | (2006.01) | |
| *G02B 27/01* | (2006.01) | |
| *G06F 1/16* | (2006.01) | |
| *G06F 3/0481* | (2013.01) | |
| *G16H 40/63* | (2018.01) | |
| *G16H 10/60* | (2018.01) | |
| *G16H 10/65* | (2018.01) | |
| *G06Q 50/22* | (2018.01) | |
| *G06F 3/147* | (2006.01) | |
| *G06F 9/451* | (2018.01) | |

(52) U.S. Cl.
CPC ......... *G06Q 50/22* (2013.01); *G09G 2354/00* (2013.01); *G09G 2370/16* (2013.01); *G09G 2380/08* (2013.01)

(56) References Cited

U.S. PATENT DOCUMENTS

| | | | | |
|---|---|---|---|---|
| 9,282,826 | B1* | 3/2016 | Hickman | A47C 7/54 |
| 2005/0122312 | A1* | 6/2005 | Huang | G06F 3/03543 |
| | | | | 345/163 |
| 2012/0206322 | A1* | 8/2012 | Osterhout | G02B 27/0093 |
| | | | | 345/8 |
| 2012/0231903 | A1* | 9/2012 | Drozjock | A63B 69/0002 |
| | | | | 473/422 |
| 2014/0222526 | A1* | 8/2014 | Shakil | G06Q 50/22 |
| | | | | 705/7.38 |
| 2015/0269324 | A1 | 9/2015 | Sherman | |
| 2015/0290494 | A1* | 10/2015 | King | A63B 71/0622 |
| | | | | 482/8 |

* cited by examiner

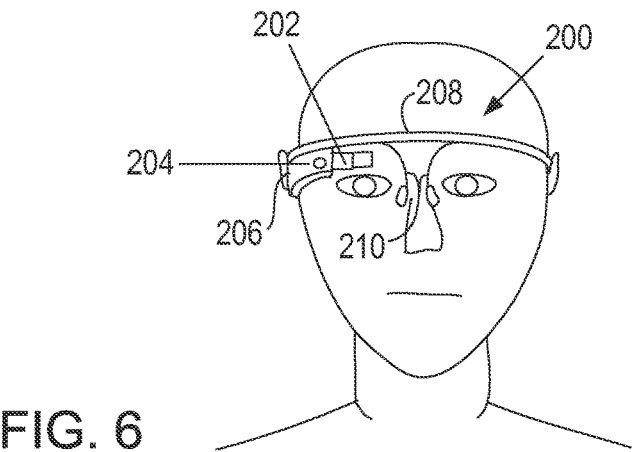
FIG. 6
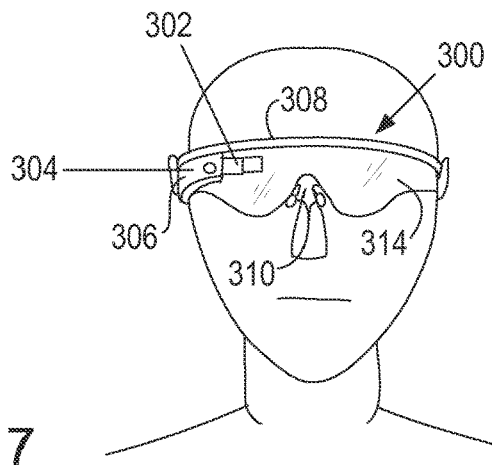
FIG. 7
FIG. 8
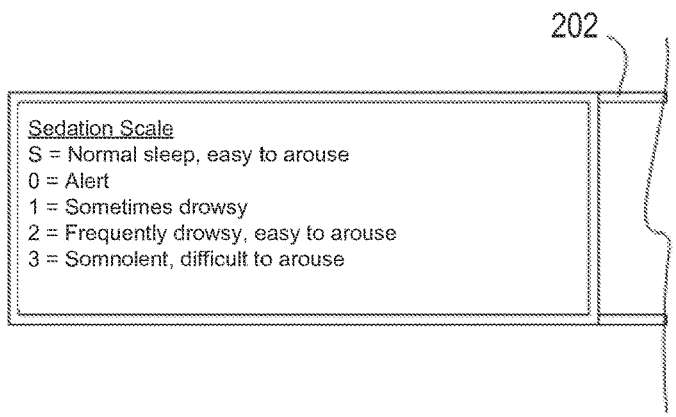

PERIPHERAL NERVE BLOCK PROTOCOL – SINGLE INJECTION AND CONTINUOUS INFUSION

Anesthesiologist Procedure Note:

<patient name>, a <patient age> year old <patient sex> was referred to the department of anesthesia for a xxxx femoral nerve block with catheter insertion in order to provide postoperative pain relief.

Please refer to surgeon's history/physical and operative note for medical and surgical history.

Informed consent was obtained during the pre-anesthetic evaluation. Risks and possible complications were explained in detail including intravascular injection, hematoma and rare nerve damage. Patient understands and wishes to proceed.

A surgical procedure was performed uneventfully under spinal anesthesia with intrathecal narcotic. This procedure was performed post-operatively in PACU. Spinal level has recovered to S-3 (sensory) with full bilateral lower extremity motor control recovery.

After a brief review of systems and the patient's chart, correct site was verified. The patient is placed in the supine position with slight abduction and external rotation of the xxxx leg. A line is drawn between the xxxx anterior superior iliac spine and the pubic tubercle, identifying the inguinal ligament. The femoral artery is identified with ultra-sound. The injection site (~2cm caudad to the inguinal ligament and ~1cm lateral to the femoral artery) was marked. After sterile prep and drape, 1% lidocaine local anesthetic was injected. An 18-guage, 100 mm short-bevel tuohy needle was inserted and advance under ultra-sound guidance until a paresthesia was elicited using nerve stimulation. Upon determination of maximal stimulation response with minimal current, a 19-guage catheter was then inserted and the needle withdrawn. The catheter was stimulated again to confirm placement close to the nerve bundle and after careful aspiration, xxxx of xxxx xxxx was injected slowly with intermittent aspiration. The catheter was then secured with a sterile op-site dressing and stat lock securing device. The patient tolerated the procedure well and experienced adequate pain relief in the anterior aspect of the xxxx knee. The femoral nerve catheter was placed on an infusion pump infusing xxxx at a rate of xxxx at xxxx . The patient was discharged from the PACU in satisfactory condition.

Parameters Monitored: blood pressure; pulse; respiratory rate; oxygen saturation; pain severity (pain scale: 0=no pain - 10=worst pain); pain location ( list of suggested locations or other - verbally named); sensation assessment (present/absent, anterior/posterior/medical/lateral, thigh/knee/leg/foot); sensation scale (2, 1, 0); sedation level (S, 0, 1, 2, 3); motor function (2, 1, 0); signs of local anesthetic toxicity or side effects (yes/no, if yes - verbally add); and general assessment.

Frequency of Monitoring: single injection - every hour over four hours, then every four hours over twenty-four hours or until discharge; infusion - every hour over four hours, then every four hours for duration of infusion, and upon discontinuation of infusion every four hours over twenty-four hours or until discharge.

General Assessment: position of blocked extremity (anatomic position description/pressure points padded/knee propped on pillow); catheter site assessment (dressing clean and dry/drainage present or absent/color description of drainage); status of catheter (in place and functioning/dislodged or nonfunctioning); blocked extremity peripheral pulse (present/absent); blocked extremity color description; blocked extremity skin assessment (example: warm, dry, free of pressure ulcers or other lesions); patient communication; communication with other healthcare provider; intervention (change or adjustment based on healthcare provider communication, patient condition, response, reaction etc.).

Medication Documentation: medication name, route, rate of infusion, concentration of infusion, dose; dosage adjustments; Infusion bag change; Injection dose amount; Cumulative dose if PCA mode in use; Verification check of orders on arrival to nursing unit; Independent double check performed for changing infusion bag (yes/no); Verification of mode and rate of infusion (specify example; continuous mode at 10 mL/hr.); progress note (healthcare provider dictated notes on patient presentation, findings, progress, response to treatment, assessment, plan etc.).

FIG. 9

FACILITATING USER INPUT VIA ARM-MOUNTED PERIPHERAL DEVICE INTERFACING WITH HEAD-MOUNTED DISPLAY DEVICE

CROSS-REFERENCE TO RELATED APPLICATION

For purposes of the United States, the present application is a continuation of, and claims the benefit under 35 U.S.C. § 120 to, U.S. nonprovisional patent application Ser. No. 14/473,894 filed Aug. 29, 2014, which '894 application is a nonprovisional patent application of, and claims the benefit under 35 U.S.C. § 119 to, U.S. provisional patent application 61/884,344 filed Sep. 30, 2013. The disclosure of this provisional patent application is incorporated by reference herein and is set forth in the Appendix hereto and incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to methods and apparatus for user data entry and, in particular, to methods and apparatus for recording and documenting observed data and, in preferred embodiments, such methods and apparatus are used by healthcare professionals in the healthcare context for recording and documenting observed data regarding patients.

Further in this respect, a patient conventionally receives healthcare from multiple medical and paramedical healthcare professionals over time, including by way of example, and not limitation, physicians, nurses, nurse practitioners, nursing assistants, and physical therapists. The healthcare is generally provided through a series of observation-intervention interactions between each healthcare professional and the patient, and data regarding such interactions is observed and recorded by the healthcare professional in the patient's electronic healthcare record so as to provide a comprehensive record of the patient's health and the healthcare provided to the patient over time.

Such comprehensive recording and documenting of observed data by a healthcare professional has drawbacks to the extent that the time required to record and document such observed data detracts from the time that a healthcare professional otherwise could spend with patients. For example, a nurse's function is largely divided into two broad categories of activities, comprising: patient contact and professional interaction; and, charting and medical recordkeeping. Approximately half of the time spent by nurses is dedicated to just charting and medical recordkeeping. This is believed to be largely due to the sequential nature of these activities, insofar as the charting and recordkeeping usually occur after the patient contact and professional interaction.

It is believed that improvements can be realized in the provision of healthcare by performing such activities in parallel rather than in series. One or more embodiments of systems, methods and apparatus in accordance with one or more aspects and features of the present invention are believed to represent such improvements.

SUMMARY OF THE INVENTION

The present invention includes many aspects and features. Moreover, while many aspects and features relate to, and are described in, the context of patient care in the healthcare industry, the present invention is not limited to use only in such context, as will become apparent from the following summaries and detailed descriptions of aspects, features, and one or more embodiments of the present invention. Indeed, one or more embodiments of the present invention are applicable in any field requiring human observation and recording of data.

Accordingly, one aspect of the present invention relates to data entry by a user. Specifically, in a first aspect, an apparatus for performing data entry by a user comprises: a first electronic device configured to be attached to a person's head and comprising a display for viewing by the person; and a second electronic device configured to be attached to a person's forearm. The second electronic device is used in combination with the first electronic device. In this respect, the first and the second electronic devices are configured to wirelessly communicate with each other, at least some of the wireless communications representing user input by the person for interfacing with a user interface displayed to the person on the display of the first electronic device, whereby data entry by the person is accomplished. The first electronic device further is configured for wireless communications with a computer system whereby data entered by the person is wirelessly transmitted to the computer system for electronic storage in a non-transitory computer readable medium.

In a feature of this aspect, the first and the second electronic devices are paired and communicate using a Bluetooth standard.

In a feature of this aspect, the observed data wirelessly transmitted to the computer system comprises healthcare information relating to a patient, and the healthcare information is stored in an electronic healthcare record of the patient.

In another aspect, an apparatus for performing data entry by a user, comprises: a first electronic device configured to be attached to a user's head and comprising a display for viewing by the user; and a second electronic device configured to be attached to a user's arm and used in combination with the first electronic device, the first and the second electronic devices being configured to wirelessly communicate with each other, at least some of the wireless communications representing user input by the user for interfacing with a user interface displayed to the user on the display of the first electronic device, whereby data entry by the user is accomplished. Furthermore, the first electronic device is configured to use the display to visually prompt a user wearing the device to enter data regarding an object of observation, interaction, or both by the user. The first electronic device is configured to receive from the second electronic device the data and wirelessly transmit the received data to a computer system (such as a server) over a computer network (such as an intranet or the Internet).

In another aspect, an arm-mounted electronic device for use as a wireless peripheral device comprises: (a) an attachment portion configured for attachment of the device to an arm, including a forearm, a wrist, or both; (b) a palm control portion containing circuitry and electronic components for performing functions and providing electronic capabilities of the device; and (c) an adjustable extension arm extending between and supporting the palm control portion relative to the attachment portion.

In a feature of this aspect, the attachment portion comprises straps for wrapping around or otherwise encircling the arm, including a forearm or wrist of a person.

In a feature of this aspect, the straps comprise hook-and-loop fasteners for customized attachment and adjustment to an arm.

In a feature of this aspect, the palm control portion comprises a contoured surface for generally abutting a palm of a hand when in use, and an opposite surface that is generally planar.

In a feature of this aspect, the palm control portion comprises surface areas that are touch-sensitive, whereby user input is received when a finger or thumb touches or taps a particular touch-sensitive area of the palm control portion.

In a feature of this aspect, the extension arm is retained to the attachment portion by a support that defines an opening through which the extension arm slides. In some embodiments, an end of the extension arm comprises an enlarged peripheral area that exceeds the dimensions of the opening defined by the support such that the peripheral area acts as a stop limiting the extent to which the extension arm slides relative to the support.

In a feature of this aspect, the extension arm is secured to the attachment portion and is able to swivel or rotate relative to the attachment portion for minor angular adjustment of the control portion relative to the attachment portion.

In a feature of this aspect, the palm control portion is movable between an extended position and a retracted position relative to the attachment portion.

In a feature of this aspect, the extension arm includes a hinge mechanism providing hinge type articulation by which the control portion can be rotated about 180 degrees, the extension arm folding back on itself from an extended, "in use" position to a folded, stowed position.

With further regard to this feature, in some embodiments the hinge mechanism is located near a base of the palm control portion, and the attachment portion includes one or more magnets that attract and retain the palm control portion to the attachment portion when the extension arm is in the folded, stowed position. Further in this respect, in some embodiments the one or more magnets serve to deactivate input controls of the palm control portion when the palm control portion is retained to the attachment portion by the one or more magnets.

In a feature of this aspect, the device further comprises an optical device configured to read a bar code. The data read may be an identification for a patient for confirmation of a person to receive healthcare service at the time and place of service.

In a feature of this aspect, the device further comprises a wireless transceiver or wireless receiver for reading an RFID tag, or reading a similar wireless electronic identification device. The data read may be identification for a patient for confirmation of a person to receive healthcare service at the time and place of service.

In a feature of this aspect, the palm control portion contains one or more application specific integrated circuits or ASICs; a non-transitory computer-readable medium; processor for executing computer-readable instructions contained in such medium; and associated computer components including a system bus and operating system; or combination thereof.

In another aspect of the invention, a head-mounted electronic device for performing data entry by a user comprises:

(a) a display for viewing by the person, wherein the device is configured to use the display to visually prompt a user wearing the device to enter data regarding an object of observation, interaction, or both by the person, and wherein the device is configured to receive user input representing the data; and (b) one or more wireless communication components configured to wirelessly transmit the entered data to a computer system for electronic storage in a non-transitory computer readable medium of a computer system.

In a feature of this aspect, the object is a patient receiving healthcare service from a person wearing the device.

In a feature of this aspect, the device is paired with a hand-operated wireless peripheral input device for receiving user input from the person representing the data regarding the object of observation, interaction, or both by the person.

In another aspect, a head-mounted electronic device for performing data entry by a user comprises: (a) a display for viewing by the person, wherein the device is configured to use the display to visually prompt a user wearing the device to enter data regarding an object of observation, interaction, or both by the person, and wherein the device is configured to receive user input representing the data; and (b) one or more wireless communication components configured to wirelessly transmit the entered data to a computer system for electronic storage in a non-transitory computer readable medium of a computer system. Furthermore, the device also comprises a camera configured to capture one or more images of the object of observation or of the interaction of the person with the object, and wherein the wireless communication components are further configured to wirelessly transmit the captured one or more images to the computer system for electronic storage in a non-transitory computer readable medium of the computer system.

In a feature of this aspect, the device further comprises a housing containing components of the camera as well as other electronics of the device, including electronics supporting operation of the display.

In a feature of this aspect, the device further comprises eyeglasses.

In another feature, the device further comprises goggles.

In another feature, the device comprises personal protective eyewear.

In another feature, the device comprises a lens. Furthermore, the camera may be integrated into the lens.

In another feature, the camera is aligned with a line-of-sight of a person when the device is positioned on the person's head.

In another feature, the device comprises a band that extends from ear-to-ear and includes supports for positioning of the band on and relative to the person's nose.

In another feature, the device is configured to take still frame photographs.

In another feature, the device is configured to take video.

In another feature, the device is configured to take video as well as to take still frame photographs.

In another feature, a brightness of the display is adjusted according to ambient light, as sensed by the head-mounted electronic device.

In another feature, the head-mounted electronic device further comprises a rechargeable power supply; one or more wireless receivers and one or more wireless transmitters, or one or more wireless transceivers; an integrated microphone for receiving and processing the voice of the person wearing the device; a gyroscope sensor for detecting spacial orientation of the device; and an auditory communication component for providing audible communications—either through the auditory canal or bone conduction—to a person wearing the head-mounted electronic device.

In another feature, the device further comprises night vision technology for use in low light environments for digital facial recognition as well as photography and videography.

In another feature, the device comprises telecommunication capabilities—including voice and data.

In another feature, the device is configured to receive and respond to voice commands and take dictation from a person wearing the device.

In another aspect, a method for performing data entry by a user comprises using the head-mounted electronic device of a foregoing aspect and entering the data using the head-mounted electronic device in real time as the observation or interaction is occurring.

In another aspect, a method for performing data entry by a user comprises using the arm-mounted electronic device of a foregoing aspect in conjunction with the head-mounted electronic device of a foregoing aspect, and entering the data using the arm-mounted electronic device in real time as the observation or interaction is occurring.

In another aspect, a system in which users perform data entry includes each user performing data entry using the head-mounted electronic device of a foregoing aspect, and entering the data using the head-mounted electronic device in real time as the observation or interaction is occurring.

In yet another aspect, a system in which users perform data entry includes each user performing data entry using the arm-mounted electronic device of a foregoing aspect in conjunction with the head-mounted electronic device of a foregoing aspect, and entering the data using the arm-mounted electronic device in real time as the observation or interaction is occurring.

In features of the foregoing two aspects, the data entered by each user relates to a patient and wherein the data is saved in the patient's electronic healthcare record.

In this respect, a user preferably performs a credential verification process before data entry can be performed. Furthermore, the credential verification process comprises an identification verification process, and the identification verification process preferably comprises two-factor authentication.

Additionally, the data entry is facilitated by use of one or more protocols, which may be identified upon admission of the patient to a healthcare facility or upon diagnosis of the patient and implementation of a treatment plan.

In a feature of one or more of the foregoing aspects, a head-mounted electronic device is further configured to wirelessly interface with other devices that automatically acquire data, and is configured to wirelessly transmit the data from the other devices to the computer system for electronic storage in a non-transitory computer readable medium of the computer system.

In a feature of one or more of the foregoing aspects, a head-mounted electronic device is configured such that the act of inverting the device locks the device from use until a person is authenticated for data entry using the device.

Other aspects include systems in which data of a patient is acquired and stored in an electronic healthcare record of the patient in accordance with one or more of the foregoing aspects and features.

Still other aspect and features are disclosed in the provisional patent application from which priority is claimed, which is found in the Appendix, and which is incorporated herein by reference.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings.

FIG. 6 is a schematic illustration of a front elevational view of a head-mounted electronic device being worn by a person in accordance with one or more aspects and features of the present invention.

FIG. 7 is a schematic illustration of a front elevational view of another head-mounted electronic device being worn by a person in accordance with one or more aspects and features of the present invention.

FIG. 8 illustrates information that is shown on a display of a head-mounted electronic device following a verbal cue by the wearer.

FIG. 9 schematically illustrates a document for an exemplary protocol for a peripheral nerve block procedure, including single injection and continuous fusion.

DETAILED DESCRIPTION

Figure 1:
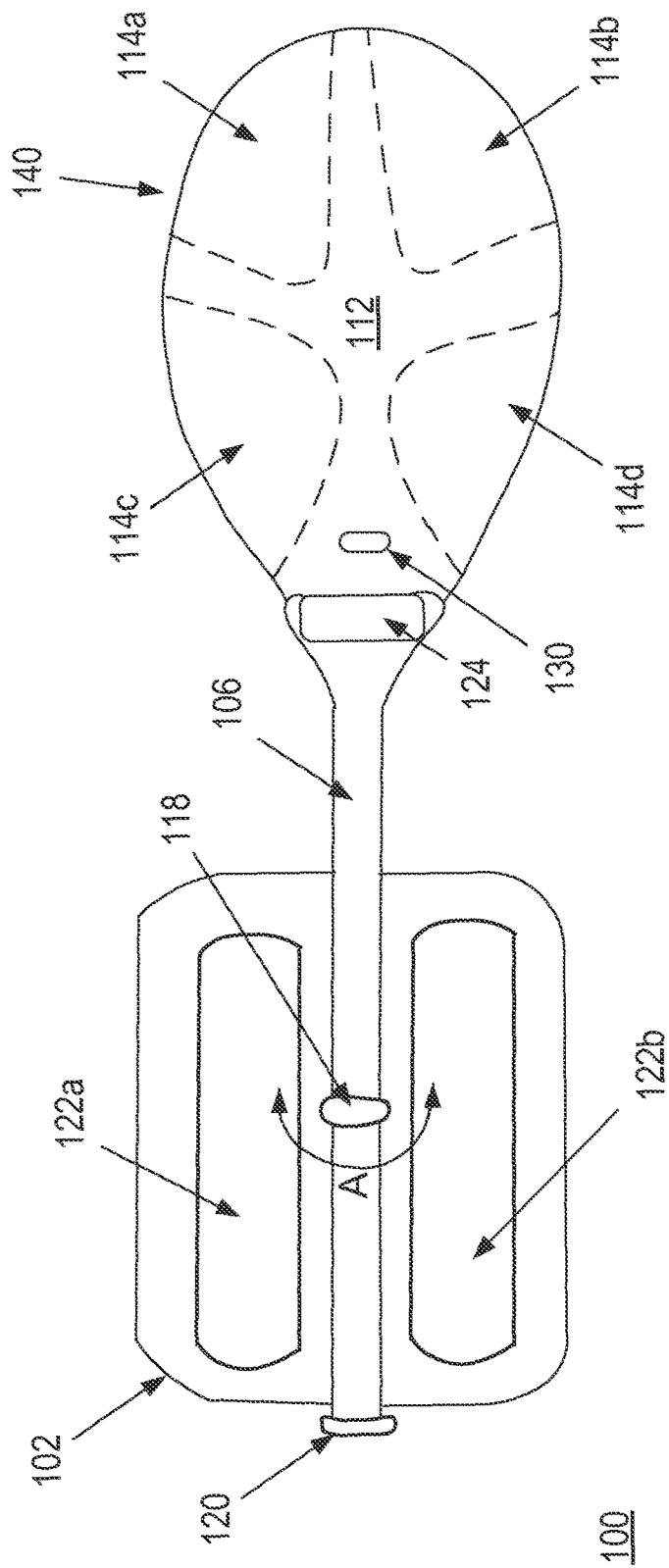
FIG. 1 is a schematic illustration of a bottom plan view of an arm-mounted electronic device in accordance with one or more aspects and features of the present invention.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described.

The following description of one or more preferred embodiments is merely exemplary in nature and is in no way intended to limit the invention, its implementations, or uses.

A preferred apparatus in accordance with one or more aspects and features of the invention comprises a head-mounted electronic device used in combination with an arm-mounted electronic device. An exemplary arm-mounted electronic device is described below with reference to FIGS. 1-5, and an exemplary head-mounted electronic device is described below with reference to FIG. 6. Another alternative exemplary head-mounted electronic device is described below with reference to FIG. 7.

Arm-Mounted Electronic Device

Figure 2:
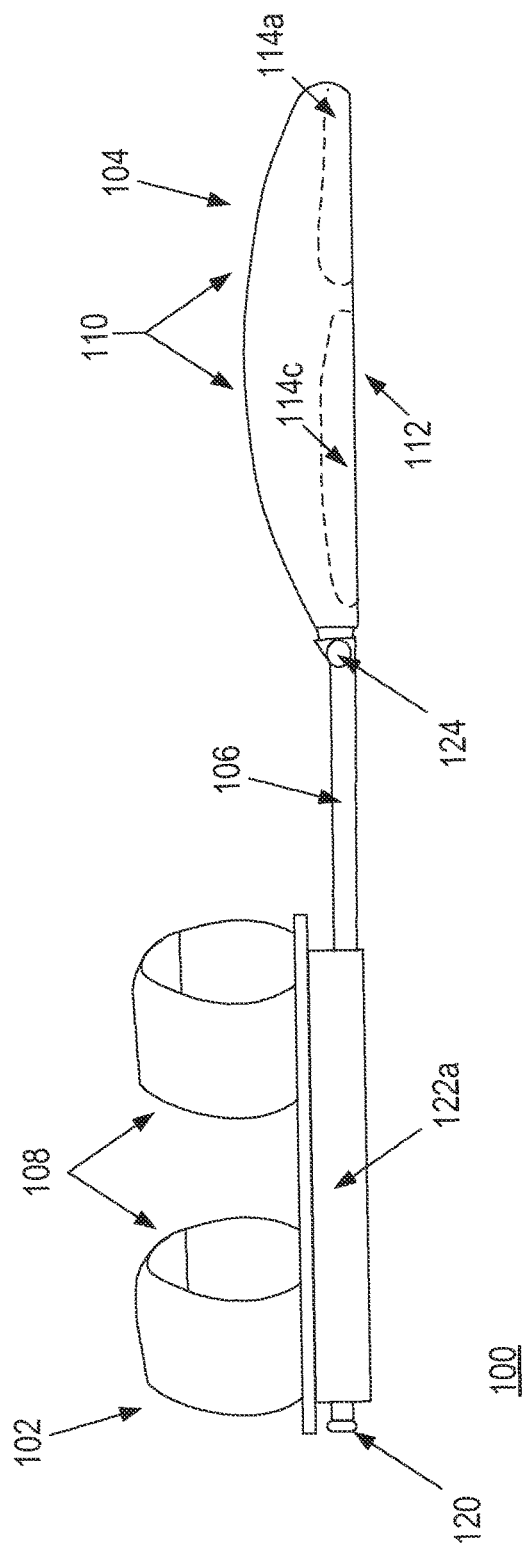
FIG. 2 is a schematic illustration of a side elevational view of the arm-mounted electronic device of FIG. 1.
Figure 3:
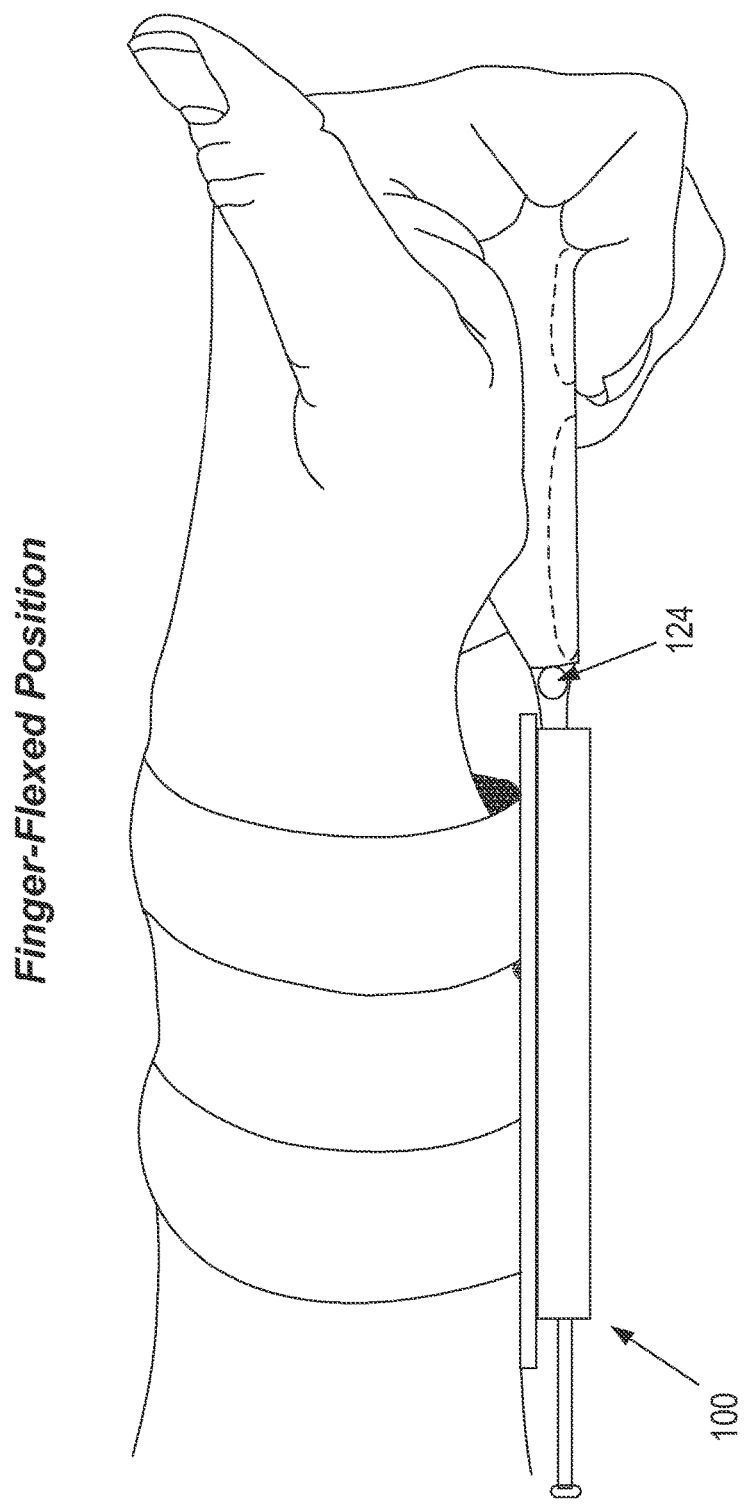
FIG. 3 is a schematic illustration of a side elevational view of the arm-mounted electronic device of FIG. 1 when mounted on an arm with the hand in a finger-flexed position.
Figure 4:
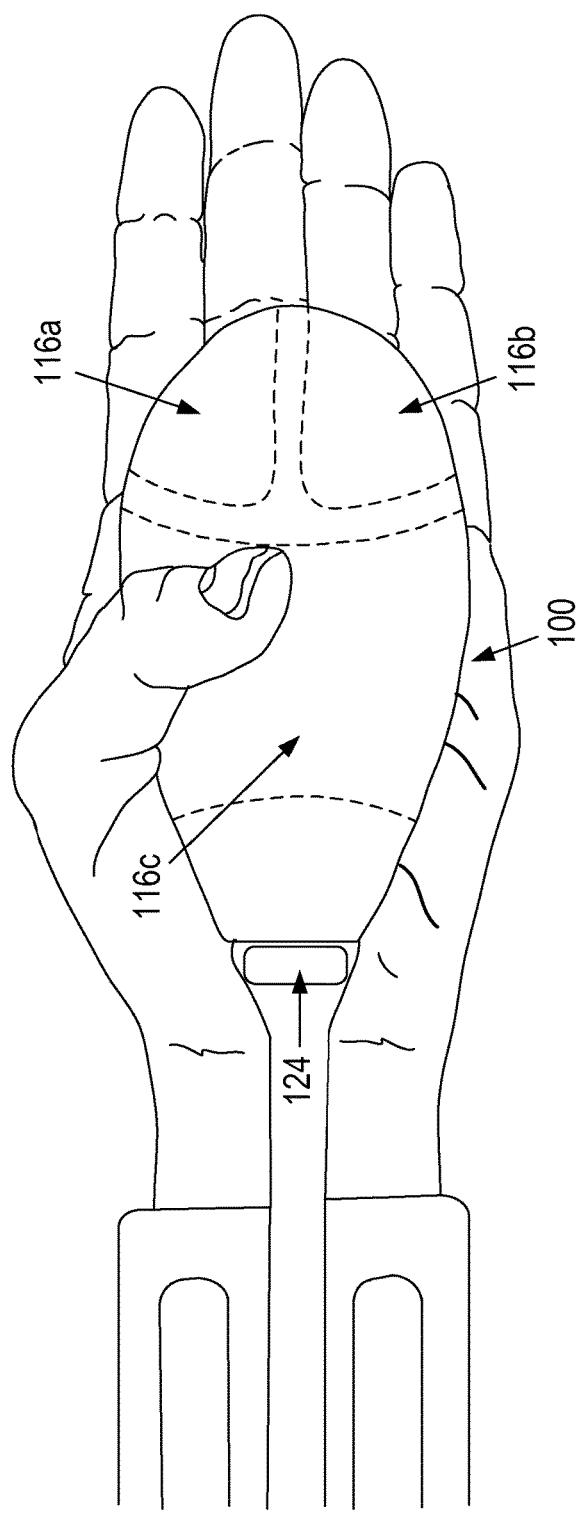
FIG. 4 is a schematic illustration of a bottom view of the arm-mounted electronic device of FIG. 1 when mounted on an arm with the thumb in a thumb-control position.
Figure 5:
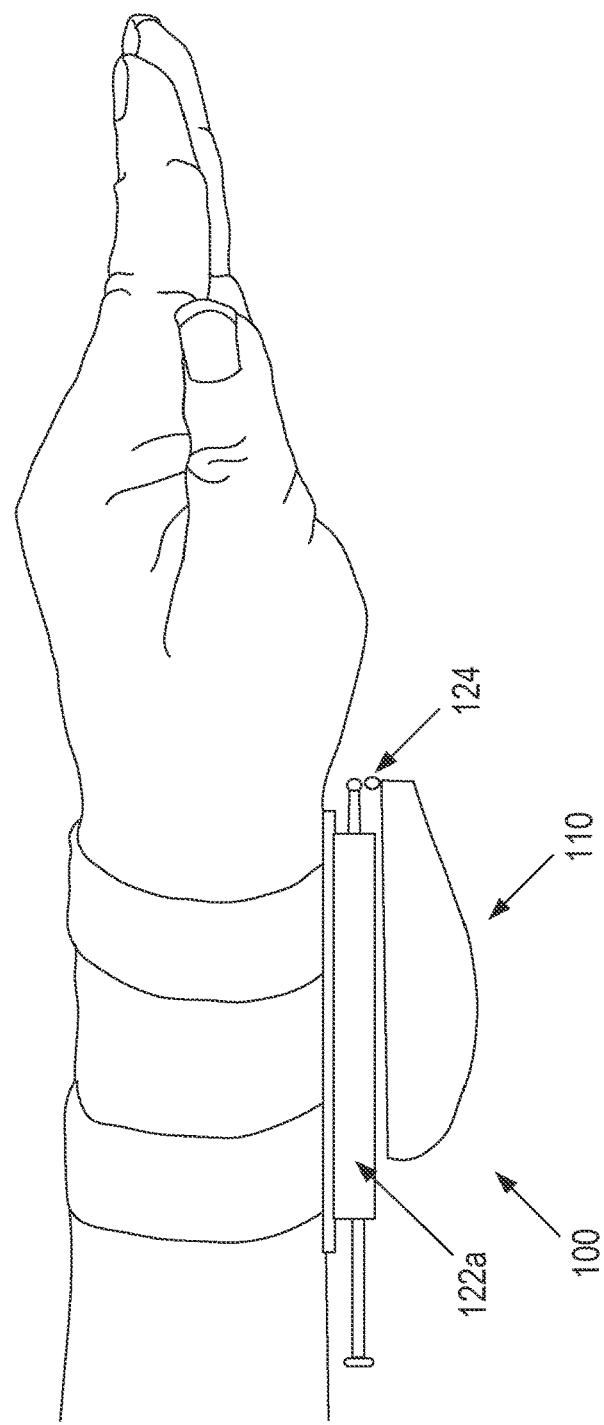
FIG. 5 is a schematic illustration of a side elevational view of the arm-mounted electronic device of FIG. 1 when mounted on an arm with the device in a stowed configuration.

With respect first to the arm-mounted electronic device, a bottom plan view of an arm-mounted electronic device 100 in accordance with one or more aspects and features of the present invention is schematically illustrated in FIG. 1, and a schematic illustration of a side elevational view thereof is provided in FIG. 2. Furthermore, a side elevational view of the arm-mounted electronic device 100 is illustrated in FIG. 3, wherein the device 100 is shown mounted on an arm with the hand in a finger-flexed position; a bottom view of the arm-mounted electronic device 100 is illustrated in FIG. 4, wherein the device 100 is shown mounted on an arm with the thumb in a thumb-control position; and a side elevational view of the device 100 is illustrated in FIG. 5, wherein the device 100 is shown mounted on an arm with the device in a stowed configuration.

As illustrated, the arm-mounted electronic device 100 comprises attachment portion 102 for attaching the device to either a forearm or a wrist of an arm; a palm control portion 104; and an adjustable extension arm 106 extending between and supporting the palm control portion 104 relative to the attachment portion 102 such that the palm control portion will rest in the palm of a hand or at the fingertips when the device 100 is used. In more detail, the attachment portion 102 preferably includes straps 108 for wrapping around or otherwise encircling a forearm and/or wrist of a person, as perhaps best shown in FIG. 3. The straps 108 may include hook-and-loop fasteners for customized attachment and adjustment to a particular forearm and/or wrist.

The control portion 104 preferably includes a contoured surface 110 for generally abutting a palm of a hand when in use. An opposite surface 112 of the control portion 104 is preferably generally planar, as perhaps best shown in FIG. 2. Areas 114a,114b,114c,114d of the surface 112 preferably are touch-sensitive, whereby user input is received by the arm-mounted electronic device 100 when a finger or thumb touches or taps a particular area 114a,114b,114c,114d of the surface 112. While four touch-sensitive areas are shown in FIGS. 1-2, a different number and configuration of touch-sensitive areas can be provided instead. For instance, three touch-sensitive areas 116a,116b,116c can be provided, as illustrated in FIG. 4. The touch-sensitive areas preferably are configured to provide tactile distinction for non-visual differentiation by touch. These areas further can be visually demarcated as part of an aesthetic appearance of the device, if desired.

In alternative embodiments, or in addition to the touch-sensitive areas, a scroll control is provided. The scroll control may be in the form of a scroll wheel, or a touch sensitive area that sense and reacts to sliding in similar manner to the scroll wheel. Such scroll control functionality and mechanisms are conventionally known and found, for example, in the mouse (PC and Mac) peripheral and in the track pad.

The extension arm 106 extends between and supports the control portion 104 relative to the attachment portion 102. In particular, the extension arm 106 preferably is retained to the attachment portion 102 by a support 118 that defines an opening through which the extension arm 106 is able to slide. An end of the extension arm 106 includes an enlarged peripheral area 120 that exceeds the dimensions of the opening defined by the support 118 such that the peripheral area 120 acts as a stop limiting the extent to which the extension arm 106 may slide through the opening defined in the support 118. Additionally, the support 118 preferably is able to swivel or rotate relative to the attachment portion 102 as illustrated at A in FIG. 1 for minor angular adjustment of the control portion 104 relative to a hand when the attachment portion is secured to a user's forearm and/or wrist, thereby providing a better fit and greater comfort during use. In particular, the palm control portion 104 is designed to be at fingertip level using the thumb for control input or retracted into the palm of the hand with fingers flexed for fingertip control input.

In view of the foregoing descriptions, it will be appreciated that the device 100 is illustrated in FIGS. 1, 2, and 4 with the extension arm 106 in a partially retracted position relative to the support 118. In contrast, the device 100 is illustrated in FIGS. 3 and 5 with the extension arm 106 in a greater retracted position relative to the support 118. It will further be appreciated that the device 100 is usable in the retracted position as well as in the partially retracted or extended position, depending on the portion of the forearm and/or wrist to which the attachment portion 102 is secured when used.

The extension arm 106 preferably includes a hinge mechanism 124 near a base of the palm control portion 104 providing hinge type articulation by which the control portion 102 can be rotated about 180 degrees, folding back on itself from the "in use" position, as shown in FIG. 2 for example, to a "stowed" position at the point of attachment either at the wrist or forearm, as shown in FIG. 5. Furthermore, the attachment portion 102 preferably includes walls 122a,122b containing one or more magnets that attract and hold the control portion 104 in the stowed position of FIG. 5. In addition to storing the palm control portion 104 out of way of the person's hands, the magnets also deactivate input controls of the palm control portion 104.

In addition to the foregoing, the device 100 preferably comprises an optical device 130 for reading a bar code. The device 100 alternatively may include a wireless transceiver or receiver for reading an RFID tag or similar wireless electronic identification device. In the exemplary implementation described herein, the identification is that for a patient for confirmation of the person receiving healthcare service at the time and place of service.

The control portion 104 preferably contains circuitry and other electronic components for performing the functions and providing the electronic capabilities of the arm-mounted electronic device described herein. In this respect, the control portion 104 preferably includes circuitry such as one or more application specific integrated circuits or ASICs; a non-transitory computer-readable medium, processor for executing computer-readable instructions contained in such medium, and associated computer components including a system bus and operating system; or combination thereof.

Head-Mounted Electronic Device

The head-mounted electronic device preferably is lightweight, comfortable to wear on one's head, and allows unobtrusive communication by the person wearing the device with another person.

With reference to device 200 shown in FIG. 6, a front elevational view of the device 200 being worn by a person in accordance with one or more aspects and features of the present invention is schematically illustrated. The head-mounted electronic device 200 comprises a band 208 that extends from ear-to-ear and includes supports 210 for positioning of the band 208 on and relative to the person's nose. The head-mounted electronic device 200 also preferably comprises a display 202 providing a head-mounted display for view by the person, and a camera 204 preferably having both still frame and video capabilities. Preferably, a brightness of the display 202 is automatically adjusted according to the ambient light sensed by the head-mounted electronic device 200.

The camera 204 is aligned with the line-of-sight of the person when the device 200 is positioned on the person's head. A housing 206 contains the components of the camera 204 as well as other electronics of the device 200, including the electronics supporting operation of the display 202. Those electronics include a rechargeable power supply, such as a rechargeable source; one or more wireless receivers and one or more wireless transmitters, or one or more wireless transceivers; an integrated microphone for receiving and processing the voice of the person wearing the device 200; a gyroscope sensor for detecting spacial orientation of the device 200; and auditory communication component for providing audible communications—either through the auditory canal or bone conduction—to the person wearing the device 200 (preferably through bone conduction from the device so as not to interfere with patient communications or the use of a stethoscope while wearing the device 200). It is further contemplated that, in a low light environment, the head-mounted electronic device 200 may incorporate and utilize night vision technology for digital facial recognition as well as photography and videography.

The head-mounted electronic device alternatively may be fashioned in the form of eyeglasses or low profile goggles that serve as personal protective eyewear (PPE), as shown in FIG. 7, wherein a front elevational view of an alternative head-mounted electronic device 300 in the form of goggles being worn by a person in accordance with one or more aspects and features of the present invention is schematically illustrated. Similar to device 200, the head-mounted electronic device 300 comprises a band 308 that extends from ear-to-ear and includes supports 310 for positioning of the band 308 on and relative to the person's nose. The head-mounted electronic device 300 also preferably comprises a display 302 providing a head-mounted display for view by the person, and a camera 304. Preferably, a brightness of the display 302 is automatically adjusted according to the ambient light sensed by the head-mounted electronic device 300.

The camera 304 is aligned with the line-of-sight of the person when the device 300 is positioned on the person's head. A housing 306 contains the components of the camera 304 as well as other electronics of the device 300, including the electronics supporting operation of the display 302. Those electronics include a rechargeable power supply, such as a rechargeable source; one or more wireless receivers and one or more wireless transmitters, or one or more wireless transceivers; an integrated microphone for receiving and processing the voice of the person wearing the device 300;

a gyroscope sensor for detecting spacial orientation of the device 300; and auditory communication component for providing audible communications—either through the auditory canal or bone conduction—to the person wearing the device 300 (preferably through bone conduction from the device so as not to interfere with patient communications or the use of a stethoscope while wearing the device 300). The lens 314 may be of any color, but preferably are clear for better eye-to-eye communication between the person wearing the device and the person with whom that person interacts. Furthermore, the display 302 preferably is integrated with the lens 314 in a location that is offset from a direct forward line of sight of the person wearing the device 300. It is further contemplated that, in a low light environment, the head-mounted electronic device 300 may incorporate and utilize night vision technology for digital facial recognition as well as photography and videography.

In addition to the foregoing, it is also contemplated that the head-mounted electronic device may include any sensors or other electronic components and include any capabilities that are conventionally found in an iPhone 5s, including for example, one or more accelerometers, ambient light sensing capabilities, and telecommunication capabilities—including voice and data. The head-mounted electronic device also preferably is configured to receive and respond to voice commands and take dictation from a person wearing the device.

Interaction of Arm-Mounted Electronic Device and Head-Mounted Electronic Device

In accordance with one or more aspects and features of the present invention, the arm-mounted electronic device is used to interface with and control the head-mounted electronic device. In this respect, the arm-mounted electronic device preferably includes a wireless receiver and transmitter, or transceiver, for two-way communications with the head-mounted electronic device whereby the arm-mounted electronic device serves as a peripheral for user input for the head-mounted electronic device. For example, a Bluetooth communications link can be established between the arm-mounted electronic device and the head-mounted electronic device, wherein touch-sensitive areas of the control portion—when touched—generate signals that are wirelessly communicated to the head-mounted electronic device as user input. Indeed, for example and by analogy, the touching or tapping once of the area 114a shown in FIG. 1 could be equated to a single click of a right mouse button, and touching or tapping once the area 114b shown in FIG. 1 could be equated to a single click of a left mouse button. It will be appreciated that, in this respect, the arm-mounted electronic device constitutes a hand-operated wireless peripheral device of the head-mounted electronic device.

In addition to or apart from use of the arm-mounted electronic device, it is contemplated that the head-mounted electronic device can be used to directly receive user input without the arm-mounted electronic device. Such user input may be accomplished by voice; by inclusion of one or more touch-sensitive areas on the head-mounted electronic device itself, such as at one or more areas of the surface of housing 206 or housing 306; the inclusion of buttons or other controls for manual actuation; and any combination of the foregoing; however, the arm-mounted electronic device preferably is used during dialogue with a patient to facilitate more natural appearing interaction with the patient, as opposed to having to touch the head-mounted electronic device to provide user input.

Exemplary Use of Head-Mounted Electronic Device in Recording and Documenting Observed Data in Healthcare Context It is believed that the head-mounted electronic device can be effectively and efficiently used in methods and systems for recording and documenting observed data in a healthcare context so as to achieve substantial cost and time savings over conventional methods and systems. It is believed that efficiency improvements will result from real time, simultaneous data collection and recording during the actual provision of healthcare service to a patient, thereby avoiding much of the charting and documenting that is conventionally done after a patient is seen. Within such context, data entered by the user during a patient encounter preferably is recorded in the patient's electronic healthcare record of a conventional EHR software system. The following is an example of such contemplated use of the head-mounted electronic device.

To begin, a person dons the head-mounted electronic device on his or her head and attaches the arm-mounted electronic device to his or her preferred arm. The person then performs a credential verification process to insure the person is authorized to enter data and, moreover, is authorized to enter the particular type of data to be entered. In this respect, the person preferably must go through an identification verification process in order for the person to be authorized to observe and document healthcare information regarding the patient. Preferably, two-factor authentication is used including combination of biological and/or non-biological identifications.

As an example of a non-biological authentication, the person wearing the head-mounted electronic device enters an identifier of an authorized person and a password associated with the authorized person. The password preferably is entered using the display of the head-mounted electronic device, which preferably enables a person to scroll through and select, using the arm-mounted electronic device, a series of letters, numbers, and symbols constituting the password. Preferably, voice is not used in providing a password for security purposes; furthermore, using the head-mounted electronic device in conjunction with the arm-mounted electronic device eliminates the risk of keystroke visualization by an observer.

As another example, authentication using biologic identification may include facial recognition using a mirror, hand recognition, or voice recognition, among others. Voice recognition, for instance, preferably starts with a unique system generated sentence, phrase or word that is displayed to the suspect person wearing the head-mounted electronic device for reciting. In this respect, the "system" preferably comprises one or more computers or servers with software configured to interact with and support the head-mounted electronic device as described herein, as well as interact with conventional software for maintaining, updating, and retrieving electronic healthcare records of patients. The system preferably includes wireless communication capabilities for real time, concurrent wireless communication with the head-mounted electronic device during use by the person.

Upon being presented with the system-generated sentence, phrase or word, the suspect person then reads the displayed sentence or phrase aloud, and the system analyzes the tone and speech pattern against known tone and speech patterns of the person purported to be wearing the head-mounted electronic device. Using a unique, system generated phrase or sentence for voice analysis adds security by eliminating universal commands that can be generated or replicated fraudulently. Once a person's identity is verified, all observed and documented data is credited to the person. Timestamps, including date and time, preferably also are associated with the observed and documented data.

Next the subject must be identified that will be the object of the observation and data gathering. In the healthcare example chosen, the subject is the patient. Preferably, two forms of identification are used to identify and authenticate the patient before any data is recorded or documented. Any combination of non-biological and/or biological identifiers can be used.

For example, a patient's wristband generally will include, among other things, a machine-readable bar code representing a patient ID. In this scenario, a patient's wristband can be scanned using the optical reader of the arm-mounted electronic device, with the data read therefrom being communicated to the head-mounted electronic device and then communicated to the system for identification. In response, a resulting identification of a patient then preferably is communicated back to the head-mounted electronic device for reference.

Facial recognition of the patient then can be used to authenticate the identification. In this regard, the camera of the head-mounted electronic device takes an image of the face of the patient and communicates the image to the system, and an identification is communicated back to the head-mounted electronic device for reference; the identification communicated back may comprise a name or patient identifier corresponding to a matching reference image, or an indication of whether the image sent corresponds to a reference image as identified by a first identification of the patient, such as the patient ID read from the patient wristband. A reference image—or other reference biological information—of the patient preferably is obtained during patient registration. Thus, in this example, the patient ID identifies the patient and the facial recognition process authenticates the identification of the patient. It is contemplated that facial or other anatomic identifying algorithms can be used.

After identification and authentication of the person using the head-mounted electronic device and identification and authentication of the patient, the healthcare service is rendered by the person to the patient. Preferably, the healthcare service provided is at least partially scripted insofar as notes to be taken, parameters to be monitored, frequency of monitoring, general assessment, and medication information to be documented are all specified in a predefined document in the system. For example, a document for an exemplary protocol for a peripheral nerve block, including single injection and continuous fusion, is schematically illustrated in FIG. 9. This information can be contained in a database or other form of data storage for ready access and use.

With respect to the exemplary protocol of FIG. 9, it will be appreciated that the "Anesthesiologist Procedure Note" contains a predefined template for use by an anesthesiologist when performing the procedure of the protocol wearing a head-mounted electronic device in accordance with one or more aspects and features of the present invention. When the template is used to create the note, certain patient healthcare data taken from the identified and authenticated patient's electronic healthcare record is prepopulated in the note, such as for example, the patient's name, age, and gender, which preferably is obtained from the patient during patient registration. This type of data is represented by the placeholders shown between the angle brackets in courier new font the template in FIG. 9.

Once populated, the information in the note is shown on the display of the head-mounted electronic device during the procedure. The person performing the procedure and wearing the head-mounted electronic device at least in some embodiments preferably reads aloud the text of the note while performing the procedure, thereby confirming the information in the note while concurrently performing the procedure. If at any time the process needs to be suspended; for example in order to respond to a question, this can be accomplished either verbally or manually. A unique, specific command not commonly used in the verbal text is employed for this purpose, and predefined manual user input received via either the arm-mounted electronic device or the head-mounted electronic acts as a device pause/resume button.

Of course, it will be appreciated that certain information will not be predefined and will be included in the note by the person providing the healthcare service. Placeholders are provided for insertion of this type of information into the note by the person providing the healthcare service while performing the service. These placeholders—or option points—are represented with "xxxx" and shown in bold and underline in the template of FIG. 9. The option points appear within the body of the text for selection choices, such as medication injected or infused, total volume injected, rate of infusion, complication, etc., and each option point will be cued and entered in real time.

Using the integrated microphone of the head-mounted electronic device, cueing of the option point for data entry preferably is prefaced by a predefined system keyword or keywords, such as for example "cue", followed by the specific key word(s) representing the data being entered. Such predefined system keyword(s) aids the system in avoiding misinterpretation of the same word(s) used elsewhere in the protocol and/or in different context. For example, stating "cue pulse" will cue the system and the key word "pulse" will blink in the display, indicating that the system is ready to receive data representing the patient's pulse. The data will then be verbalized, for example by saying "eighty two". A verbal pause of 3-5 seconds then preferably will close the data entry point and the parameter will stop blinking. The duration of the pause after data entry and until the entry point closes can be adjusted depending on a user's preference.

As another example, a person might say, "cue sedation scale". The options for this parameter would then appear on the display of the head-mounted electronic device, and the person could then make a selection using a touch-sensitive input or verbal command. Accordingly, predefined options can be presented when appropriate from which a person can select the data to be entered, and where appropriate no predefined options are presented and/or data that is not predefined or part of a menu for selection can provided by the person.

It will further be appreciated that some symbols will be used as part of the displayed data and will be recognized verbally. For example, "cue blood pressure" will open the blood pressure data entry point. Example data entry then would be spoken as, "one twenty over eighty". This entry would be represented as 120/80. This will be appreciated as an example of how the system preferably recognizes spoken symbols throughout the program in proper context based on commonly used nomenclature.

Preferably, if a voice command is not recognized, then an alert is given indicating to the user that the voice command was not recognized. Such alert may be visual, auditory, or both. An exemplary visual alert comprise a blinking light shown in the display of the head-mounted device. An exemplary audible alert comprises a specific sound earmarked for use when a voice command is not recognized.

Nonverbal cueing also can be provided. For example, it is contemplated that touching a touch-sensitive area of the arm-mounted electronic device or a touch-sensitive area of the head-mounted device can trigger cueing; and positioning of the head in a predefined manner, or sequence of movements of the head, while wearing the head-mounted electronic device, as detected using the integrated gyroscope, can trigger cueing. Additionally, it is contemplated that one's eye can be monitored by the head-mounted device such that looking in a direction relative to forward that is abnormal will trigger cueing, such as looking to the outside corner of one's eye socket, or looking toward one's nose. A sequence of such glances can similarly be used as a way to trigger nonverbal cueing by the wearer of the head-mounted device.

Preferably, when data is selected or otherwise entered, a timestamp is associated with the entered data. Furthermore, the identification of the person performing the manual data entry, as identified and authenticated, is recorded in association with the entered data. Such information can be used later for, among other things, auditing, performance metrics, research, discovery and evidence in litigation, and benchmarking. Additionally, when a progress note or other transcription or documentation is made, the category of the system user is recorded in addition to the identification of user and timestamp.

Figure 10:
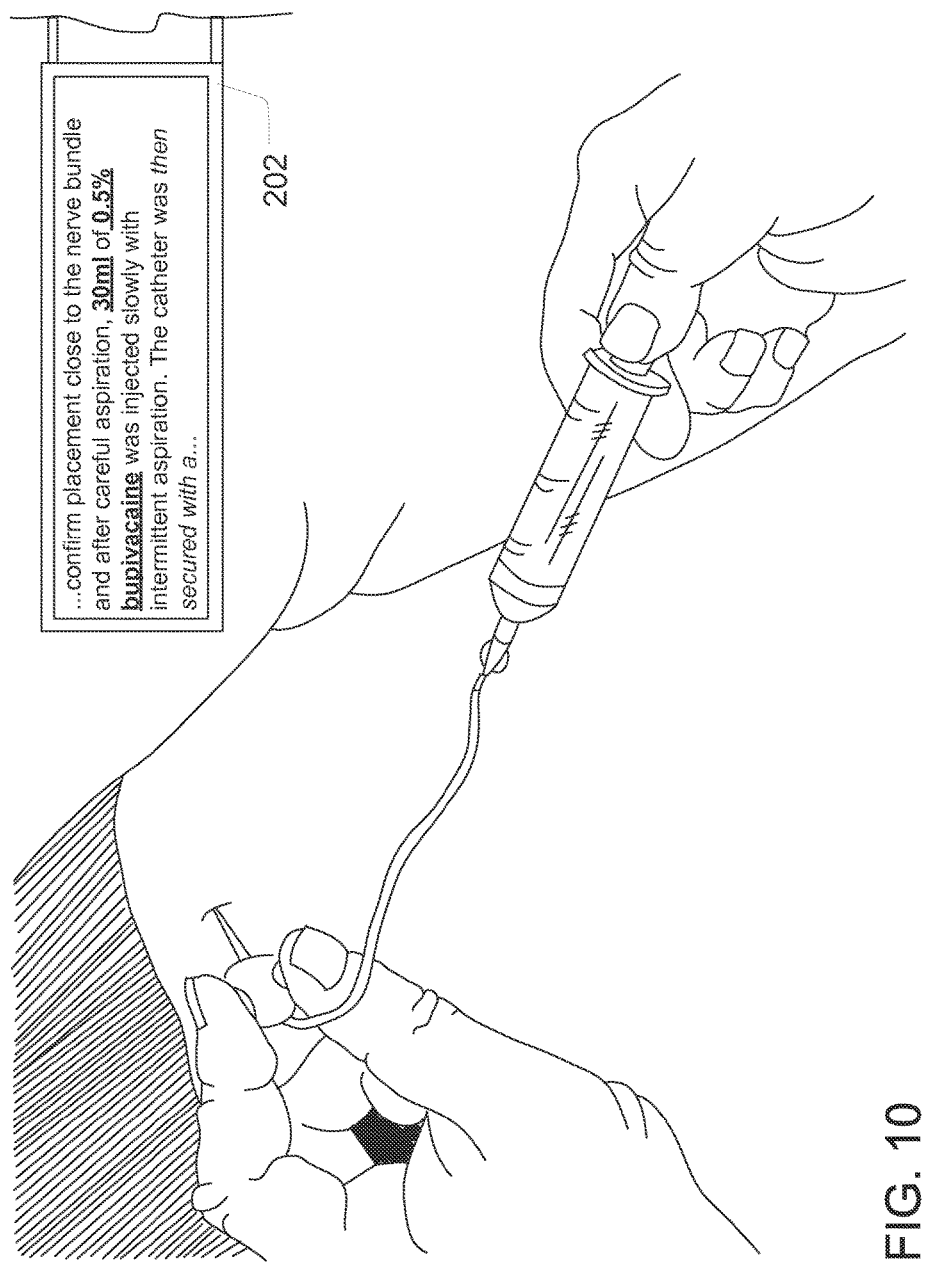
FIG. 10 illustrates a view by a person wearing a head-mounted electronic device while performing the procedure of the protocol of FIG. 9.

FIG. 10 illustrates a view by a person wearing a head-mounted electronic device while performing the procedure of the protocol of FIG. 9. As illustrated, the person reads the text while performing the procedure. In this example, the displayed text changes from italics to non-italics as the text is read, thereby prompting the person to read next the first italicized word seen. Furthermore, the head-mounted electronic device is configured to take still frame photographs and/or video as the procedure is performed and store the data as part of the patient's electronic healthcare record for later reference, if and when needed. Examples of such usage in the healthcare context include sequential photographs documenting wound healing or video by physical therapy documenting patient ability or progress. Such recordings can be taken automatically or upon command of the person wearing the head-mounted electronic device.

With continuing reference to FIG. 10, it will be appreciated that the display is located in the upper right-hand portion of the person's view and does not lie directly in the line-of-sight of the person; alternatively, the display could be located in the upper left-hand portion of the person's view. The display reflects that point of progress for the procedure being performed. Preferably, the user through a series of specific commands is able to advance or track back the displayed portion of the text of the note.

In some preferred embodiments, in which the text of the note is not read while performing the procedure, the option points are still cued and data entered by the person while performing the procedure. Furthermore, in the case of a sterile medical procedure, such as the one in the exemplary protocol describe above, verbal data entry is most likely preferred and the arm-mounted electronic device may not be used by the person providing the healthcare service.

It will be appreciated that the above example protocol is a specific protocol chosen by, for example, an ordering physician, and a number of healthcare professionals are involved in the protocol, namely, the anesthesiologist as well as one or more nurses, nursing assistants, and pharmacists. The portions of the protocol pertaining to each such person preferably are routed by the system to the appropriate persons and, through a head-mounted electronic device of each person, a single coherent electronic healthcare record is created in real time including all of the pertinent data observed and documented together with a consolidated, chronological ordering of the events that transpired.

For example, a timestamp corresponding to the start of the infusion preferably is recorded by the system, and used to trigger subsequent workflows. A pharmacist subsequently preferably receives notification on his or her head-mounted electronic device to prepare and deliver infusion to the patient's nurse at a predefined time before the next infusion is due. The notice is sent by the system based on the time the infusion was started, the rate of infusion, and the total volume of infusion, as recorded and documented in real time in the patient's electronic healthcare record. As an example, when 0.2% bupivacaine infusion was started at 14:10, with a total infusion volume of 250 mL and a rate of 10 mL/hr, then the system calculates that the infusion will last 25 hours, and notice is provided to the pharmacist 24 hours after the start of the infusion. In this case, notice to the pharmacist will be sent at 14:10 the following day.

The foregoing protocol is an example of one of many that can be created and implemented. Moreover, appropriate protocols preferably are selected and combined for a particular patient, such as upon admission to a hospital or upon diagnosis of a condition and implementation of a treatment plan. For example, where a patient is admitted for a total knee replacement, several protocols preferably are identified for carrying out by appropriate healthcare providers, including for example a general medical doctor, a surgeon, an anesthesiologist, nurses, nursing assistants, and a physical therapist. Furthermore, each healthcare provider will have a range of protocols to choose and apply as determined to be most appropriate for the individual patient based on the professional judgment of the provider. For example, the surgeon may choose a general surgical protocol, or an orthopedic protocol, or a more refined orthopedic protocol specifically for total knee replacement. The anesthesiologist may choose a continuous femoral nerve catheter protocol for post-operative pain control, similar to the exemplary protocol described herein with reference to FIG. 9. Protocols preferably are activated or deactivated in the system at any time by authorized persons in their professional judgments. The system further preferably coordinates tasks contained in each applied protocol so that tasks are not duplicated and redundancy is eliminated.

It will be appreciated that the data collected from each person by way of that person's head-mounted electronic device is integrated to create a coherent patient electronic healthcare record. For example, both the surgeon and anesthesiologist protocols may require nursing assistants to collect patient vital signs every three hours. The system recognizes this, eliminates redundancy, and gives a single command notification to a nursing assistant at the appropriate time for collecting the patient vitals. The system further accommodates unique task commands in addition to predefined protocols and tasks therein. For example, a physician can add an order not found in the protocol. In this respect, the physician adds the task, specifies the parameters, and identifies the category of user to carry out the task. For example, a physician may add zolpidem 10 mg to be taken by mouth at bedtime as needed for insomnia, specifying the user category as nursing. The system would thereafter alert nursing at the appropriate time of the physician's order, preferably incorporating the order and due time in the listing of patients for a responsible nurse.

User-friendly features preferably form part of each protocol design. For example, a person using a head-mounted electronic device preferably is able to view, with a simple verbal command, a list of all parameters for which data is to be entered by that person during a protocol, such as "cue main menu", whereupon the list of such parameters appears. Preferably, the predefined system keyword(s) for cueing a particular parameter are shown in the list, preferably in bold, whereby the person may cue a selected parameter for entry of the data for the selected parameter. Furthermore, currently due parameters preferably are visually differentiated from parameters not currently due. For example, parameters currently due may appear in red and those parameters not currently due may appear in black or another color, and time urgency may be visually displayed by a slow blinking text, such as when a parameter has not been addressed thirty minutes or longer after its due time.

In another example of a user-friendly feature, definitions used in the system preferably are easily referenced with a simple voice command. For example, a person might say "cue definition sedation scale", the result for which appears on the display 202 of the head-mounted electronic device 200. A resulting display as might be seen is shown in FIG. 8.

It is also preferred that, in at least some embodiments, a person has the option to bypass or otherwise not use the template for a procedure and, instead, enter free text.

The head-mounted electronic device also preferably is used in physician case management. In this example, a physician is able to view a list of all patients under his or her care by saying, for example, "cue my patients", whereupon a list of patients assigned to the physician is shown on the display of the head-mounted electronic device. The listing preferably identifies each patient name and current location. Furthermore, patients with currently due parameters or issues to be addressed preferably are visually differentiated from other patients, such as for example by displaying such patients in a different color or different manner. Visual differentiation can be accomplished through color differences and/or slow blinking indicating chronology or priority.

Embodiments in accordance with one or more aspects and features of the present invention also preferably enable and provide additional functionality, including: Internet connectivity for searching and retrieval of reference information for queries to things such as medical information or to better answer patient questions; translations utilizing language translation software that recognizes a spoken language and plays back or displays the translation; and identification and warning of adverse drug interactions prior to dispensing medications.

Still further, it is contemplated that the data entered by the person may be automatically supplemented with data acquired by sensors and machines. For example, such sensors and machines preferably interface with the head-mounted electronic device for electronically communicating information to the head-mounted device, which information then is included with the data entered by the user into the electronic healthcare records of the patients. In a more general sense, such electronic data collectors preferably interface with the head-mounted electronic device and system so as to add to and make more complete the user-entered data in the patient's electronic healthcare record. Data also can be supplemented from other software systems that interface with the head-mounted device, including for example conventional medication management systems such as Pyxis and Omnicell systems.

When a person is done using the head-mounted electronic device, the device is removed and placed upside down on a surface. The act of removing and inverting the device preferably locks the device from further use until a person is authenticated once again for use of the device. Locking of the device through removal and inversion preferably is detected by the integrated gyroscope within the device. Preferably, all persons authorized to use the device will be trained to remove and store the device in an inverted position when not in use.

In at least some embodiments, a camera of a head-mounted device is used to stream, either directly or indirectly, a line-of-sight view as seen by the wearer to a separate display device, such as a monitor. The streaming may be direct or may be indirect, such as through one or more routers, servers, the Internet, an intranet, or combination thereof. The user interface of the head-mounted device also is communicated from the head-mounted device to the separate display device. A person viewing the separate display device thereby is able to see a complete view of what the wearer of the head-mounted device sees, including the line-of-sight view of the wearer combined with a view of the user display of the head-mounted device. Indeed, FIG. 10 is representative of that which preferably would be displayed on the separate display device. It is believed that such an arrangement would be beneficial for example during training in use of the head-mounted device. The view streamed from the camera, the view of the user display, or both, further can be recorded for later viewing on a separate display device. Such recording can be used for training or tutorials. Such recording, if pertaining to an encounter with a patient, further can be stored in connection with the electronic healthcare record of the patient as part of the documentation or notes associated with the encounter.

In view of the foregoing, it will be appreciated that a person using one or more embodiments in accordance with one or more aspects and features of the present invention is able to perform and interact in his or her work environment as normal while seamlessly interfacing with a data entry system. Use of one or more embodiments of the present invention introduces additional knowledge, enhances interaction, and provides an enriched data record, as well as improves security, accuracy and timeliness in data observation and documentation. Furthermore, all functions can be tracked by user and chronology thereby providing increased accountability, and quality assurance measures can be followed by user specific reports detailing tasks not performed or not performed within an acceptable time frame. Indeed, the following advantages and benefits are provided by one or more embodiments in accordance with one or more aspects and features of the present invention, including but not limited to: quick data retrieval, reference information, language translations, construction and/or updating of an integrated patient electronic healthcare record in real time from multiple users, verification of qualifications for users, and positive identification of the subject from which data is observed and collected.

It will further be appreciated that one or more embodiments in accordance with one or more aspects and features of the present invention improve efficiency and accuracy in receiving and recording data in a patient's electronic healthcare record which data is observed during a patient encounter, thereby representing a technological solution to current inaccuracies and inefficiencies.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments in the healthcare context, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof. For instance, continuous radioactivity sensors may provide input to a head-mounted electronic device worn by a power plant manager as part of an integrated daily record that is electronically kept for checks and monitoring activities performed by the plant manager at a power plant.

What is claimed is:

1. A method for performing data entry, by a user, of data regarding an observation of, or intervention or interaction with, an object while the observation, intervention, or interaction is occurring, comprising the steps of:
   (a) while the observation, intervention, or interaction is occurring,
      (i) displaying, to the user on a display of a head-mounted electronic display device having a rechargeable power supply and mechanically attached to the user's head, a user interface including a visual prompt for the user to enter data regarding the observation, intervention, or interaction,
      (ii) wirelessly communicating, to the head-mounted electronic display device, by an arm-mounted peripheral electronic device having a rechargeable power supply and mechanically attached to the user's arm, a signal representing user input received from the user by the arm-mounted peripheral electronic device, and
      (iii) wirelessly receiving, by the head-mounted electronic display device, the signal as user input that is responsive to the visual prompt for the user to enter data regarding the observation, intervention, or interaction; and
   (b) wirelessly communicating, to a computer system over a computer network, by the head-mounted electronic display device, data corresponding to the responsive user input as regarding the observation, intervention, or interaction;
   (c) wherein the arm-mounted peripheral electronic device comprises,
      (i) an attachment portion by which the arm-mounted peripheral electronic device is mechanically attached to the user's arm,
      (ii) a palm control portion comprising a user input area at which the user input is received, and
      (iii) an adjustable extension arm secured to the attachment portion and extending between and supporting the palm control portion relative to the attachment portion and mechanically transitionable between,
         (A) an extended position spanning the user's wrist in order to support the palm control portion adjacent the user's palm, and
         (B) a stowed position spanning the user's wrist to support the palm control portion adjacent a user's forearm,
      (iv) wherein the extension arm is mechanically configured to swivel relative to the attachment portion for minor angular adjustment of the palm control portion when the extension arm is in the extended position.

2. The method of claim 1, wherein the head-mounted electronic display device wirelessly transmits the data regarding the observation, intervention, or interaction as healthcare information relating to a patient for storing in an electronic healthcare record of the patient.

3. The method of claim 1, further comprising storing the data regarding the observation, intervention, or interaction as healthcare information in an electronic healthcare record.

4. The method of claim 1, further comprising receiving, by the arm-mounted peripheral electronic device, user input from the user when a finger or thumb of the user touches or taps a touch-sensitive area of the palm portion.

5. The method of claim 1, further comprising retaining the extension arm of the arm-mounted peripheral electronic device to the attachment portion of the arm-mounted peripheral electronic device by a support that defines an opening through which the extension arm slides, an end of the extension arm comprising an enlarged peripheral area that exceeds the dimensions of the opening defined by the support such that the peripheral area limits the extent to which the extension arm slides relative to the support.

6. The method of claim 1, wherein the head-mounted electronic display device comprises eyewear.

7. The method of claim 1, wherein the head-mounted electronic display device comprises telecommunication capabilities—including voice and data capabilities.

8. The method of claim 1, further comprising locking the head-mounted electronic display device from being used by inverting the head-mounted electronic display device.

9. The method of claim 1, wherein one or more wireless transceivers comprise the one or more wireless receivers and one or more wireless transmitters.

10. The method of claim 1, wherein the palm control portion of the arm-mounted peripheral electronic device comprises a plurality of touch-sensitive user input areas, each user input area having tactile characteristics by which the user input areas are differentiable by touch.

11. The method of claim 1, wherein the palm control portion of the arm-mounted peripheral electronic device further comprises a scroll wheel by which user input is received by the arm-mounted peripheral electronic device.

12. The method of claim 1, further comprising using an optical device of the arm-mounted peripheral electronic device to read a bar code associated with the object of the observation, intervention, or interaction.

13. The method of claim 1, further comprising using a wireless transceiver or receiver of the arm-mounted peripheral electronic device to read a wireless electronic identification device associated with the object of the observation, intervention, or interaction for reading.

14. The method of claim 1, further comprising capturing one or more images of the object of the observation, intervention, or interaction using a camera of the head-mounted electronic display device, and wirelessly communicating the captured one or more images to the computer system over the computer network.

15. A method for performing data entry by a user of data regarding an observation of, or intervention or interaction with, an object while the observation, intervention, or interaction is occurring, comprising the steps of:
  (a) while the observation, intervention, or interaction is occurring,
    (i) displaying, to the user on a display of a head-mounted electronic display device having a rechargeable power supply and mechanically attached to the user's head, a user interface including a visual prompt for the user to enter data regarding the observation, intervention, or interaction,
    (ii) wirelessly communicating, to the head-mounted electronic display device, by an arm-mounted peripheral electronic device having a rechargeable power supply and mechanically attached to the user's arm, a signal representing user input received from the user by the arm-mounted peripheral electronic device, and
    (iii) wirelessly receiving, by the head-mounted electronic display device, the signal as user input that is responsive to the visual prompt for the user to enter data regarding the observation, intervention, or interaction; and
  (b) wirelessly communicating, to a computer system over a computer network, by the head-mounted electronic display device, data corresponding to the responsive user input as regarding the observation, intervention, or interaction;
  (c) wherein the arm-mounted peripheral electronic device comprises,
    (i) an attachment portion by which the arm-mounted peripheral electronic device is mechanically attached to the user's arm,
    (ii) a palm control portion comprising a user input area at which the user input is received, and
    (iii) an adjustable extension arm secured to the attachment portion and supporting the palm control portion, the extension arm comprising a hinge mechanism providing hinge type articulation by which the palm control portion is transitionable between being adjacent a user's palm and being adjacent a user's forearm.

16. The method of claim 15, wherein the hinge mechanism is located near a base of the palm control portion.

17. The method of claim 15, wherein the palm control portion is retained to the attachment portion by one or more magnets of the attachment portion when the palm control portion arm is adjacent a user's forearm.

18. The method of claim 17, wherein the user input area of the palm control portion is deactivated by the one or more magnets when the palm control portion is retained to the attachment portion by the one or more magnets.

19. A method for performing data entry by a user regarding an observation of, or intervention or interaction with, a patient while the observation, intervention, or interaction is occurring, comprising the steps of:
  (a) while the observation, intervention, or interaction is occurring,
    (i) displaying, to the user on a display of a head-mounted electronic display device having a rechargeable power supply and mechanically attached to the user's head, a user interface including a visual prompt for the user to enter data regarding the observation, intervention, or interaction,
    (ii) wirelessly communicating, to the head-mounted electronic display device, by an arm-mounted peripheral electronic device having a rechargeable power supply and mechanically attached to the user's arm, a signal representing user input received from the user by the arm-mounted peripheral electronic device, and
    (iii) wirelessly receiving, by the head-mounted electronic display device, the signal as user input that is responsive to the visual prompt for the user to enter data regarding the observation, intervention, or interaction; and
  (b) wirelessly communicating, to a computer system over a computer network, by the head-mounted electronic display device, data corresponding to the responsive user input as healthcare information relating to a patient for storing in an electronic healthcare record of the patient;
  (c) wherein the arm-mounted peripheral electronic device comprises,
    (i) an attachment portion by which the arm-mounted peripheral electronic device is mechanically attached to the user's arm,
    (ii) a palm control portion comprising a user input area at which the user input is received, and
    (iii) an extension arm secured to the attachment portion and supporting the palm control portion, wherein the extension arm is movable between a first position for supporting the palm control portion adjacent a user's palm, and a second position for supporting the palm control portion adjacent a user's forearm.

20. The method of claim 19, further comprising storing the data as healthcare information in an electronic healthcare record.

* * * * *